United States Patent [19]

Calfee et al.

[11] Patent Number: 4,539,992
[45] Date of Patent: Sep. 10, 1985

[54] METHOD AND APPARATUS FOR COMMUNICATING WITH IMPLANTED BODY FUNCTION STIMULATOR

[75] Inventors: Richard V. Calfee, Houston; Robert N. Bertasz, Alvin; Reese S. Terry, Jr., Freeport; Pat L. Gordon, West Columbia; Ross G. Baker, Jr., Houston, all of Tex.

[73] Assignee: Intermedics, Inc., Angleton, Tex.

[21] Appl. No.: 486,157

[22] Filed: Apr. 25, 1983

Related U.S. Application Data

[63] Continuation of Ser. No. 972,231, Dec. 22, 1978, abandoned.

[51] Int. Cl.$^3$ .............................................. A61N 1/36
[52] U.S. Cl. .............................................. 128/419 PG
[58] Field of Search ............. 128/419 PG, 903, 419 E

[56] References Cited

U.S. PATENT DOCUMENTS

| | | | |
|---|---|---|---|
| 3,562,671 | 2/1971 | Honma et al. | 375/23 |
| 3,727,616 | 4/1973 | Lenzkes | 128/419 E |
| 3,987,447 | 10/1976 | Lockhart, Jr. et al. | 375/23 |
| 4,049,004 | 9/1977 | Walters | 128/419 PG |
| 4,257,423 | 3/1981 | McDonald et al. | 128/419 PG |

Primary Examiner—William E. Kamm
Attorney, Agent, or Firm—Willian Brinks Olds Hofer Gilson & Lione Ltd.

[57] ABSTRACT

An external command device and an internal decoding and verification device are used to non-invasively alter the operating parameters of a programmable device implanted in an animal body. Thus, physiological changes can be easily accommodated by the implanted device. In a preferred embodiment, pulse position modulation is used to externally encode the command information. A resulting string of current pulses generates voltage spikes (in the internal decoding device) through inductively coupled coils. Each incoming data bit is verified and the entire command word is verified. After verification, the decoded command is transferred to a command register for simultaneously altering the selected operating parameters. The internal receiver circuitry may conveniently utilize energy from the induced voltage spike, using passive components for forming an output suitable for processing.

43 Claims, 6 Drawing Figures fig.2 fig. 3 fig.4 fig. 5 fig. 6A fig. 6B

METHOD AND APPARATUS FOR COMMUNICATING WITH IMPLANTED BODY FUNCTION STIMULATOR

This application is a continuation of application, Ser. No. 972,231, filed Dec. 22, 1978 and now abandoned.

FIELD OF INVENTION

This invention relates to commanding the operation of implanted devices, and more particularly, to programmable devices having a variety of operating parameters selectively variable in response to command signals from a noninvasive source.

BACKGROUND OF THE INVENTION

Implantable devices for controlling or monitoring various body functions represent a rapidly evolving technology. It has long been recognized that application of an electrical stimulus at a selected body location can produce a reaction by the tissue at that location. Well known examples of body function stimulators include cardiac rate pacers, bladder stimulators, phrenic nerves stimulators, and carotid sinus stimulators. Many uses are foreseen for such stimulating apparatus to either directly produce a response or to detect and control erratic stimuli produced by the body. Other implanted devices can serve as substitute organs or as monitors for detecting abnormal conditions.

It is apparent that the capability of tailoring the operating parameters of a given body stimulator to the physiological needs of the body within which the stimulator is implanted would optimize the beneficial effects of the stimulator. By way of example, cardiac pacing may require recognition and control of one or more of the following parameters:

1. Pulse rate—the pulse rate is selected from a range of rates effective to sustain life and normal activities.
2. Pulse widths—a stimulating pulse duration is selected to assure tissue response to the signal; the minimum effective pulse width generally varies as a function of such factors as myocardial fibrosis, drug therapy, and electrode selection and placement.
3. Sensitivity—the desired naturally occurring signal, generally the "QRS" complex, must be discriminable from other signal waves, such as "T" waves, to obtain proper system functioning.
4. Operating Mode—the most desirable stimulating mode of the cardiac pacer depends on the physiological status of the patient as well as the patient's environment and and a suitable mode must be selected, e.g., R-wave inhibited demand mode, R-wave synchronous demand mode, atrial-ventricular sequential demand or fixed rate mode.

It will be appreciated that physiological changes can occur even after a device, such as a cardiac pacer, is implanted such that an operating parameter change may be desired or even required to maintain effective use of the implanted device. Since modern implanted devices may be powered by a battery having a life expectancy of many years, a need has arisen to affect changes in the operating parameters without invading the body. As hereinbelow shown, the prior art has used magnetic fields and high frequency radio or other carrier signals to obtain some control over implanted cardiac pacers and other body stimulators, and has suggested transferring signals by acoustic means, light transmission, and physical pressure. The information carrying capability shown in the prior art is small, permitting limited variability. As also shown, the prior art does not provide for verifying the correctness of a received signal prior to implementing that signal. Other problems in the prior art are slow signal input, the need for a plurality of outside signals to activate a system, and/or the need for active circuits imposing a battery drain.

PRIOR ART

Early apparatus having a capability for varying an operating parameter provided a magnetically actuated reed switch in the implanted unit. Application of a magnetic field would cause the magnetic reed switch to produce an output pulse for processing by the implanted unit.

U.S. Pat. No. 3,631,860 to Lopin is illustrative of devices using a magnetic reed switch to advance a ring counter whereby the charging current to an RC timing circuit is varied to change the pulse rate. A magnet must be brought to and from a position adjacent the implanted reed switch to produce a plurality of pulses and cycle the counter. No mechanism is disclosed for discriminating against stray magnetic fields or for verifying that the information is completed before changing the pacer rate.

U.S. Pat. No. 3,805,796 to Terry, Jr. et al represents a more advanced use of magnetic reed switches to alter pacer operating parameters. The output pulses from the reed switch are provided to a counter. To protect against activation by stray signals, a count threshold must be exceeded before any change in output parameters can be effected. The Terry, Jr. et al apparatus requires that an entire cycle be completed before the counter is reset to obtain a lower count output. It is suggested that this resetting may be accomplished within a typical heart beat, but apparatus is not disclosed for accomplishing that operation. It is also suggested that communication with the implanted device may be obtained by using bursts of acoustic energy or bursts of electromagnetic energy at relatively low radio frequencies. There is no apparent teaching relative to confirmation of the input signal before effecting the operating parameter change.

U.S. Pat. No. 3,945,387 to Adams discloses yet another cardiac pacer using magnetic reed switches. The magnetic reed switch presents an enabling output to a counter which then produces a binary output in response to internal clock pulses. Adams teaches the use of a shaped magnetic pulse to prevent inadvertent operation of the clock pulse switch from stray electromagnetic fields. Adams suggests the use of light or pressure signals to activate a clock pulse switch. The counter must complete an entire cycle before resetting to a lower value and no mechanism is suggested for verifying the signal before changing the operating parameter. Adams suggests that a plurality of operating parameters might be altered using radio frequency systems tuned to a variety of frequencies for discrimination purposes.

U.S. Pat. No. 3,952,750 to Mirowski et al teaches an externally controlled implantable device for delivering cardioverting pulses. Control information is modulated onto an AC power transfer signal which is transmitted through the skin of the patient by coupled transformer primary and secondary windings. A binary control word is serially transmitted with the power transfer signal and converted to a parallel binary word for conversion to an analog signal.

U.S. Pat. No. 4,024,875 to Putzke discloses an external device for generating and transmitting a preselected number of pulses of radio frequency energy. The number of such pulses is determined by the value of the output parameter which is desired.

U.S. Pat. No. 4,066,086 to Alferness et al teaches a unit receiving an output from apparatus such as the Putzke apparatus. The pulses of radio frequency are detected, demodulated, and counted. A second externally generated signal, such as a magnetic field activating a reed switch, enables the counter to accept only a deliberate input. The output of the counter may be used to control the pulse generator repetition rate. The counter must be completely cycled before being reset and there is no mechanism for verifying the input signal before effecting a parameter change.

Several disadvantages of the above prior art are readily apparent. First, the occurrence of a stray pulse during an enabling cycle will produce an unexpected result since receipt of a correct signal is not verified. Second, only limited information can be received in a given time where a magnetic switch is actuated, e.g., almost 8200 pulses would be required for a counter system having a 12 bit binary output. Finally, the use of radio frequency or other carrier signals requires active components in the receiving apparatus which may constitute a drain on the implanted battery.

These and other disadvantages of the prior art are overcome by the present invention in support of a programmable implanted device and improved methods and apparatus are provided for generating and decoding a signal affecting a plurality of variable operating parameters.

Accordingly, it is a feature of the present invention to inductively couple externally generated pulses into an implanted device for altering the operating parameters of this device.

It is another feature that only a passive receiver is needed in the implanted device to obtain an input signal suitable for processing.

Yet another feature is verification of the processed signal before any operational parameter of the device is altered.

One other feature is detecting anamolous signals in the data signal.

An object of the present invention is to permit simultaneous variation of a plurality of operating parameters of the implanted device.

Another object is to minimize the internal energy expended by the implanted device to receive and decode a control signal.

One other object is to preclude inadvertent alteration of any operating parameter.

Still another object is to utilize only a single signal source for data transmission and verification.

SUMMARY OF THE INVENTION

A command word is non-invasively presented to an implanted device for altering selected operating parameters of the device. An external circuit generates a train of current pulses wherein binary data is represented by the spacing between pairs of adjacent pulses. The current pulses pass through a primary coil, where an edge of the current pulse generates a rapidly changing magnetic field.

The external primary coil is magnetically coupled to an implanted secondary coil to obtain a corresponding voltage spike in the secondary coil. The energy in the externally generated magnetic field determines the strength of the signal produced in the implanted circuit and passive elements may be used to form a suitable internal data pulse.

An implanted decoding circuit receives the incoming data. The temporal spacing of the incoming data is functionally equivalent to the externally encoded binary data bits. This temporal spacing is detected to form a binary control word at the output from a parallel register.

Before any stimulator output parameter is altered, the incoming data is verified. In one embodiment, each incoming data bit is generated with known signal levels at predetermined intervals. The decoded command word is further verified by transmitting a second command signal. The two command words are compared and the equivalence verified before one of the command words is transferred to the final command register for altering any of the output parameters. Then all of the operating parameters are simultaneously formed to the selected condition.

DETAILED DESCRIPTION OF THE DRAWINGS

Figure 1:
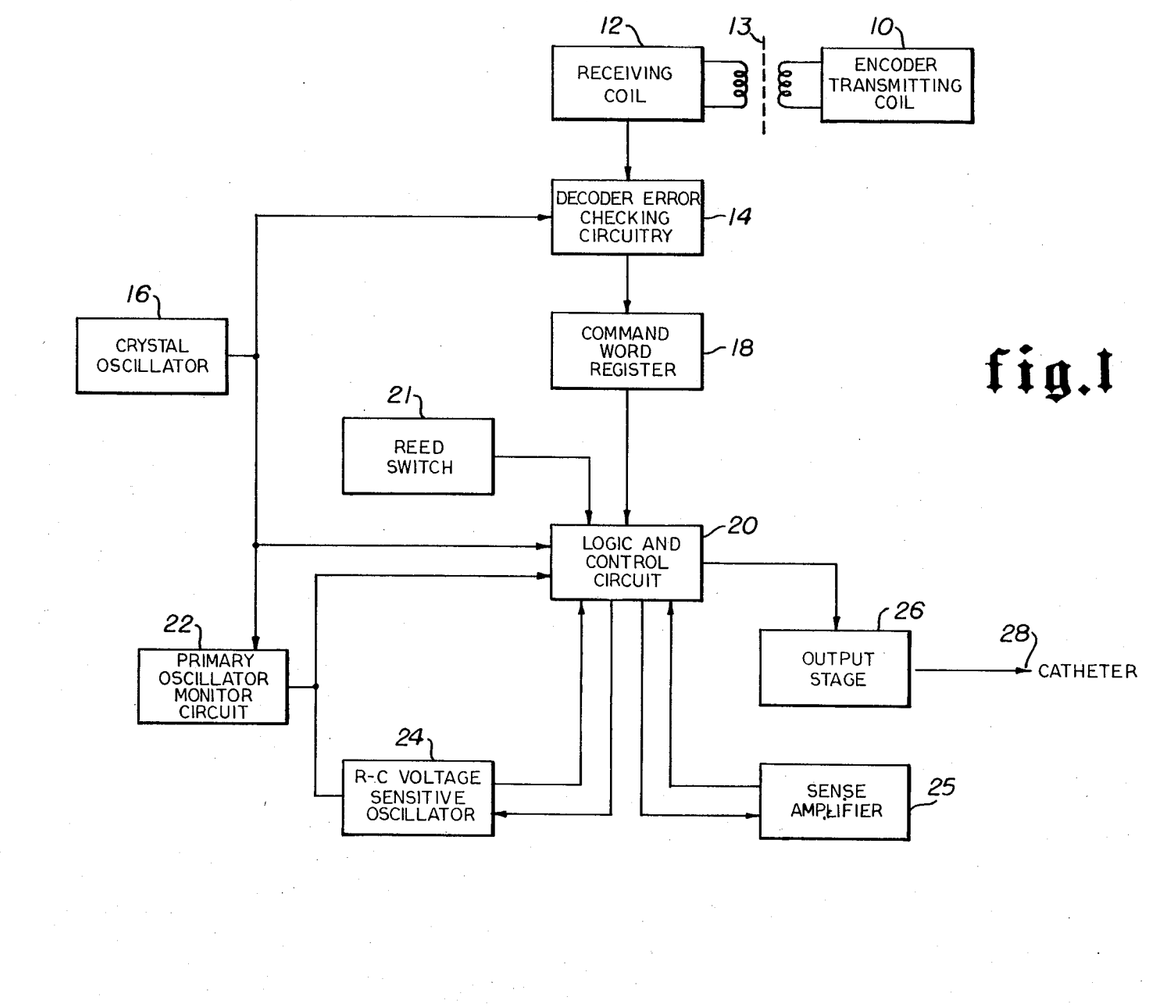
FIG. 1 is a block diagram of a programmable implantable tissue stimulator.

Referring now to FIG. 1, there may be seen in block diagram form a representation of a control system interconnected with a programmable body implantable device. The basic components for a tissue stimulating device are shown in FIG. 1 for discussion purposes. The device may be conveniently implanted in a patient at a selected location whereby the patient maintains mobility and freedom of movement. According to the present invention, apparatus is provided for altering the operating parameters of the implanted tissue stimulator without invading the patient. Thus, physiological changes in the patient may be accommodated and corrected.

A transmitting unit 10 is provided external to the patient. Transmitting unit 10 may conveniently include a keyboard for providing an input number corresponding to a selected set of stimulator operating parameters. The input may be stored in a register until it is decided to transmit the information to the implanted unit. In one embodiment, the stored information is converted to a train of position modulated pulses, converted to current pulses, and directed through a primary coil. At the trailing edge of each current pulse, the magnetic field generated during the steady state portion of the pulse rapidly decays according to conventional relationships for such an event.

As the magnetic field rapidly decays in the external coil, the decaying field generates a corresponding voltage spike in an implanted secondary coil coupled with the external coil. The primary coil and the secondary coil thus act to inductively couple information through intervening tissue, represented by interface 13. The external event occurring in transmitting unit 10 and sought to be detected is thus directly coupled into implanted unit 12 via the secondary coil.

The output from receiving unit 12 may be a train of voltage spikes, position modulated in correspondence with the external input, or some pulse shaping may be conviently done to provide a train of position modulated pulses. As hereinbelow explained, the received pulses are decoded into a command word and verified by circuitry 14 before altering the selected operating parameters of the body implanted device. In one embodiment of the present invention, each incoming data bit is sampled at selective time intervals for data verification. Further, the decoded command word may be conveniently verified by techniques such as comparing the decoded command word with a separately transmitted complement of the word.

Once the command word has been received and decoded, and the accuracy of the decoded command word verified, the command word is transferred to command word register 18. The instructions of command word register 18 are then carried out by the operational logic and control circuit 20, which may conveniently take many forms and is not a subject of the present invention.

The operation of decoder 14 and the logic and control circuit 20 may be conveniently controlled by a precision crystal oscillator 16. In some implanted devices, controlled as hereinbefore described, it may be desirable to incorporate redundant features, such as R-C voltage sensitive oscillator 24. Oscillator 24 may be directed to operate by the oscillator monitor circuit 22, which detects failure of crystal oscillator 16. Reed switch 21 may also be used to control oscillator 24.

In many applications, it is also desirable to sense body functions, either naturally occurring or produced by the stimulating pulse output. Sense/amplifier circuit 25 may be incorporated to interpret events detected by electrodes adjacent the tissue to be stimulated or monitored at other selected locations.

An operational signal is generated by logic and control circuit 20 in response to the command word in register 18, and as further directed by sense/amplifier 25 and control oscillators 16, 22 and 24. The control signal is directed to output stage 26. Reed switch 21, operated by a separate external magnetic field, may be included as a redundant feature to disenable the command circuitry when parameter changes are not desired.

Output stage 26 provides an output pulse of the selected shape and energy and delivers the output pulse to electrode means formed in catheter 28. Catheter 28 is conveniently formed to direct the stimulating and sensing electrodes to appropriate tissue portions of the patient, which may be remote from the implanted signal generator. Thus, the selected stimulating pulse is carried to the appropriate tissue and delivers the selected stimulation determined for the particular physiological needs of the patient.

It should be appreciated that the operation features hereinabove discussed for the control circuit 20, redundant oscillator 24 and monitor 22, reed switch 21, sense amplifier 25, output stage 26 and catheter 28 are not the subject of the present invention, but represent one application of the command processing system, hereinbelow described. Any number of implanted devices, such as cardiac stimulators, monitoring apparatus, or artificial organs, might be controlled according to the present invention and such applications are contemplated and considered within the scope of the present invention.

Figure 2:
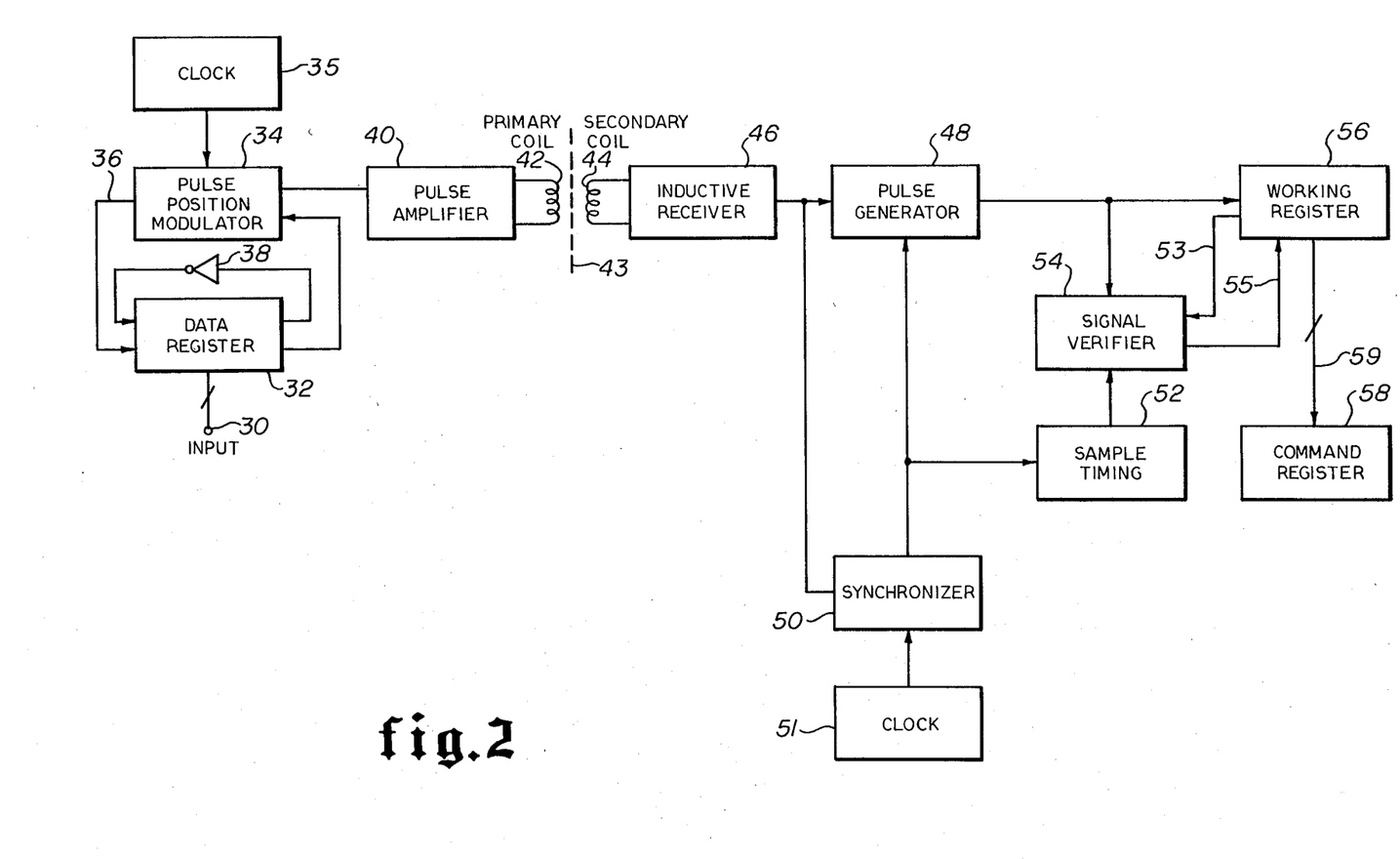
FIG. 2 is a block diagram of an encoder and implanted decoder.

Referring now to FIG. 2, there may be seen a more particular block diagram for the command system, including an external encoding apparatus inductively coupled with an internal decoding apparatus. At the external encoder, a set of desired operating parameters is selected and a control word is developed which is functionally related to the desired operating parameters. The control word may be conventionally derived from a keyboard and stored in a working register (not shown) in a binary form. The working register contents form input 30 to the encoding system.

When a suitable signal is received, input 30 is transferred to data register 32 for encoding. The digital bits in register 32 are serially transferred to pulse position modulator 34 which generates a serial pulse train having position modulated pulses. In a preferred form of pulse position modulation, the temporal spacing between adjacent pulses carries the digital information. A first temporal spacing is selected to represent a "0" and a second temporal spacing is selected to represent a "1". Clock 35 controls operation of pulse position modulator 34.

Pulse position modulator 34 also controls the operation of data register 32. Suitable control signals are provided to permit register 32 to accept either a parallel input or a serial input. In a preferred mode of operation, the data bits are serially transferred to pulse position modulator 34, and the data bits are also passed through inverter 38 and serially stored in register 32. Thus, after the original command word has been serially encoded by pulse position modulator 34, the complement of that word is stored in register 32 and is likewise encoded by pulse position modulator 34.

The position modulated pulse train may generally be composed primarily of low voltage pulses at this time. In order to use inductive coupling, however, current pulses must be formed, and pulse amplifier 40 acts to generate a train of relatively high current pulses. The current pulses are passed through primary coil 42. In one embodiment of the present invention, the trailing edge of the current pulse is used to generate a rapidly changing current across primary coil 42.

The pulse position modulation scheme is especially desirable for direct inductive coupling since the trailing edge of each pulse can be used to identify events. The trailing edge of a current pulse can be formed with a greater slope than the leading edge, producing a sharply decaying magnetic field. The ability of the pulses to transfer distinct events permits direct inductive coupling of the event to a secondary coil 44 without requiring the use of a carrier wave signal. As hereinafter used, direct inductive coupling means inductive coupling which does not require a carrier wave, such as commonly used for ordinary transformer-type coupling or radio frequency transmission.

It should be noted that primary coil 42 may be generally contained in a movable "wand" for positioning at an external location near the implanted receiver portion. Thus, primary coil 42 is inductively coupled with secondary coil 44 across the interface represented by line 43. The rapid change in the coupled magnetic field induces a voltage spike in secondary coil 44 whereby the position modulated signal is transmitted to the implanted decoder.

Voltage spikes induced in secondary coil 44 may be conveniently rectified in inductive receiver 46 for further processing. The strength of the signal received by the implanted decoder is determined by the energy input from the external system, whereby battery energy in the implanted tissue stimulator need not be used to amplify the information-containing pulse. Although state-of-the-art batteries used in implanted tissue stimulators have ever increasing lifetimes, it is important to conserve battery power in order to realize the increased lifetime. Inductive receiver 46, as hereinbelow explained, may conveniently be formed entirely from passive components.

The voltage output spike from inductive receiver 46 is passed to pulse generator 48 and to synchronizer 50. Synchronizer 50 is controlled by clock 51 and develops the timing pulses for decoding the incoming signal. Accordingly, the output pulses from synchronizer 50 go to pulse generator 48 and to sample timing circuit 52, more particularly described hereinbelow.

Pulse generator 48 is conveniently provided to form the voltage spikes into a well-defined pulse to enhance processing. In one embodiment of the present invention, pulse generator 48 also provides for first converting the position modulated pulse train into a width modulated pulse train, wherein pulse width is functionally related to the temporal spacing of adjacent data pulses.

The output from pulse generator 48 is presented to working register 56 and to signal verifier circuitry 54. Data is not accepted by working register 56 until certain signal characteristics are verified. In one convenient method, the level of the width modulated pulse from pulse generator 48 is sampled at a plurality of intervals. In a particular embodiment, the width modulated pulse will always have a preselected level at a first and third time interval and a variable level at a second selected interval functionally related to the data bit being transferred. Thus, an incoming pulse not containing the preselected level at the first and third time intervals is rejected and the command word is not accepted.

Once a complete data word is stored in working register 56, it is desirable to verify the accuracy of the decoded word prior to altering any of the output parameters. Accordingly, the encoded command word in working register 56 is returned to signal verifier circuitry 54 and verified, as hereinbelow explained. After verification, the command word is finally transferred from working register 56 as parallel input 59 to command register 58.

It is expected that the digital command word appearing at the output of command register 58 will be utilized to set the operating parameters of the implanted programmable device. There are many techniques well known in the art for converting a digital instruction to a selected operating parameter, and it is contemplated that any of the well known techniques may be used for obtaining the desired output parameter. The present invention does not contemplate or require any particular conversion circuit, and such circuitry is not within the scope of the present invention.

A preferred method of operating the system, hereinabove described, will now be set out, with particular reference to the circuit blocks depicted in FIG. 2. It should be noted that the particular command word configuration and length and the clock frequencies are selected for a particular system, and other values may be substituted in accordance with the present invention. Further, other verification methods may be used for verifying bit accuracy and command word accuracy, all within the scope of the present invention.

Once a selected set of operating parameters has been selected for the tissue stimulator, an operator might conveniently enter a set of numbers selected to represent the output parameters to form input 30. In the present embodiment, input 30 consists of 20 data bits. Clock 35 frequency is selected to be 32768 Hertz (Hz). Once the data is loaded into register 32, each data bit is serially output from register 32 to pulse position modulator 34. As hereinbelow described, pulse modulator 34 produces a pair of pulses for each data bit, wherein the spacing between adjacent pulses is functionally related to the binary state of the data bit. In the selected embodiment a "1" is represented by an interval of 16 counts, and a "0" is represented by an interval of 8 counts.

As hereinabove described, the complement of each data bit is generated and returned to the serial register 32 as each bit is transferred to pulse position modulator 34. Accordingly, after a 20 bit word has been encoded and transmitted, the complement of that word is stored in register 32 and is then encoded and transmitted for command word verification purposes. The use of the complement is preferred for positive identification purposes, although the command word itself could be transmitted twice if desired.

Each data bit generates a rapidly decaying magnetic field in primary coil 42, which produces a corresponding voltage spike in secondary coil 44. The implanted inductive receiver 46 thus receives a series of voltage spikes spaced apart according to the encoded pulse position modulation. The received voltage spike is then synchronized with the implanted decoding circuitry by synchronizer 50. Clock 51 in the implanted circuit is directed through synchronizer 50. A first incoming spike initiates an output from synchronizer 50 to pulse generator 48. The output from pulse generator 48 is a width modulated pulse, wherein the width functionally represents the temporal spacing between adjacent spikes, but wherein the timing is synchronized with clock 51.

The output from synchronizer 50 is also directed to a timing circuit 52 which samples the output level from pulse generator 48 at preselected intervals. In a selected sampling mode, an error check is made at a first and third times, which may conveniently be selected at a four count and a twenty-eight count from synchronizer 50. A total of thirty-two counts is used for receiving and verifying each data bit. As hereinbelow described, the operation of the encoding circuit in combination with the decoding circuit operates to always provide a first signal level on the four count which may conveniently be a high level, and a second signal level on the twenty-eight count, which may conveniently be a low level. Thus, each width modulated pulse will have these characteristics regardless of the actual data in the bit. An anomaly in the data bit will produce an error signal from signal verifier 54, rejecting the entire command word.

Timing circuit 52 also samples the level of the width modulated pulses at a second time, which may conveniently be the twelfth count, and enables working register 56 to accept the data level at the input to register 56. Thus, twenty bits are loaded into working register 56.

After storing the first twenty bits, a second twenty bit command word, which may conveniently be the complement of the first word, is now presented to working register 56. As hereinabove described, each bit is verified prior to loading into register 56. In addition, however, each bit of the first word is serially transferred from working register 56 for comparison with the corresponding bit of the second, verification word. Thus, the accuracy of each data bit is verified and the corresponding data bit stored in register 56. After forty data bits have been transmitted, twenty verified data bits remain in working register 56. At least a portion of these twenty data bits represent the actual command word to be used to modify the operating parameters of the implanted device.

A final verification method may be employed, using a selected number of bits having predetermined values, whereby the command word is transferred only when those values are present. Transfer of the control word requires that each data bit be verified, the decoded control word be verified, and the presence of the predetermined bits be verified. Then, and only then, is the command word transferred to the command register for changing the operating parameters of the tissue stimulation generator. It is also apparent that no operating parameter is changed until all of the command word is received and verified.

Figure 3:
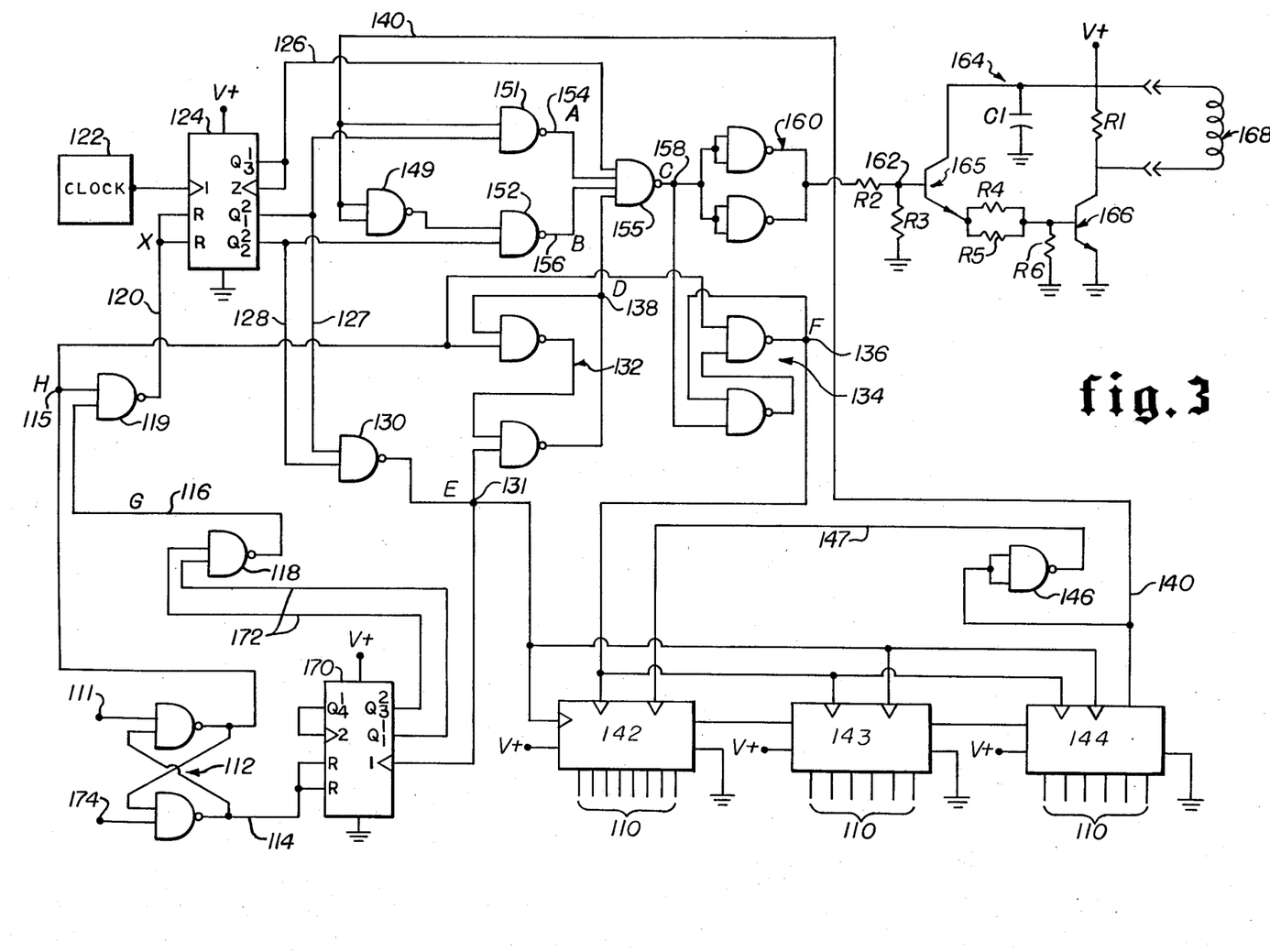
FIG. 3 is a circuit diagram of an encoder.
Figure 4:
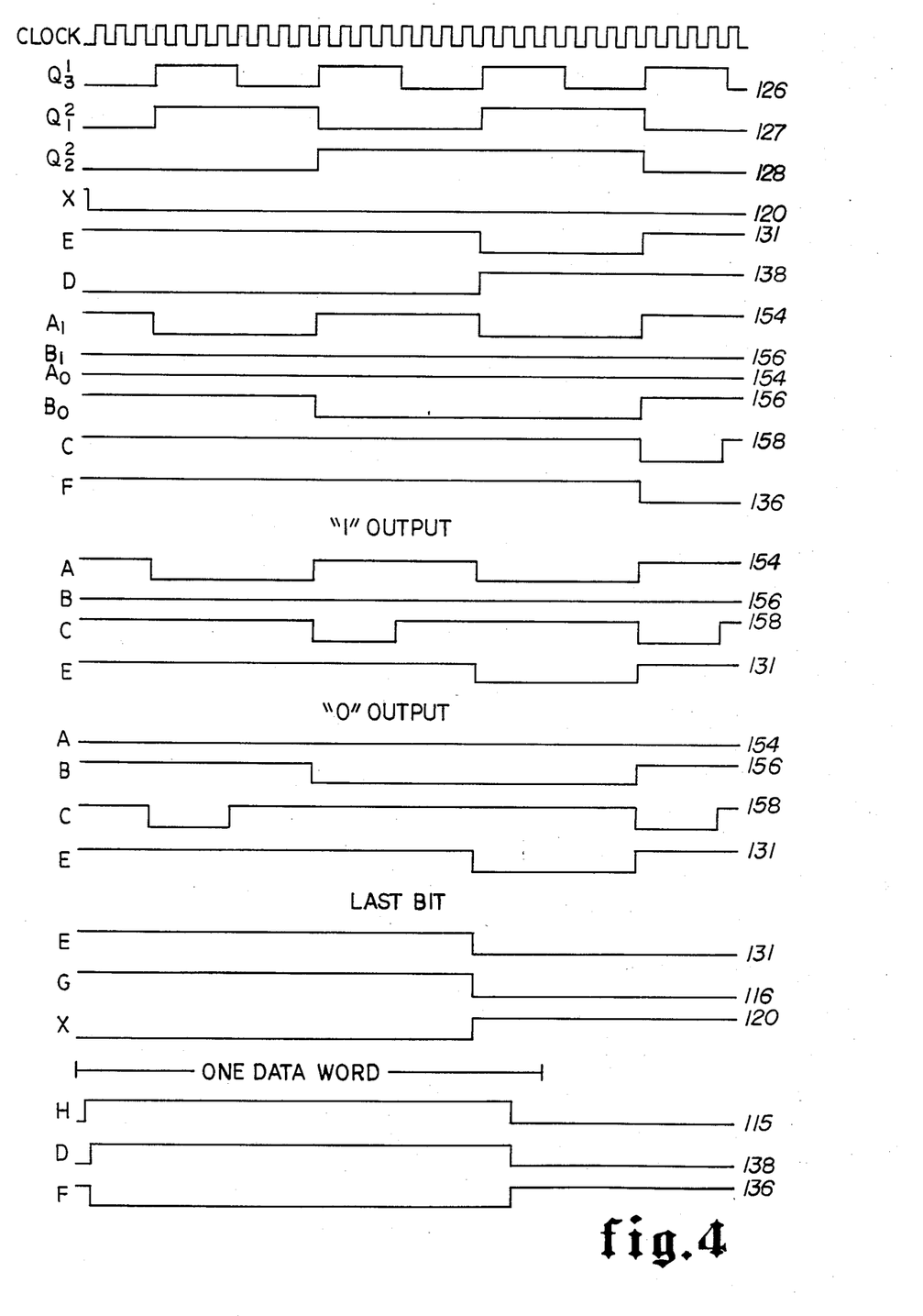
FIG. 4 is a timing diagram for selected connection in the circuit shown in FIG. 3.

Referring now to FIGS. 3 and 4, there is particular circuitry depicted in FIG. 3 for encoding an input functionally related to a selected set of operating parameters. FIG. 4 depicts the binary output at selected locations within the circuit shown in FIG. 3, and is illustrative of various encoding events, hereinafter described. In order to describe the operation of the circuit depicted in FIG. 3, it is presumed that a digital input 110 is available at the parallel loading inputs of registers 142, 143 and 144. Digital input 110 may be prepared using any conventional input keyboard and decimal-to-binary conversion circuitry to obtain a digital input functionally related to a selected set of desired operating parameters.

Encoding begins with start signal 111 to the set-reset circuit 112. Output 115 from circuit 112 goes high and remains high when start signal 111 goes low. At the same time, signal 114 goes low, removing a reset input from counter 170, the operation of which is more particularly described hereinbelow. At this time, output 116 from NAND gate 118 is high, whereby output 120 from NAND gate 119 goes low as signal 115 goes high, removing reset signal X 120 from counter 124. Signal 115 is also applied to set-reset circuits 132 and 134, which function as hereinbelow described.

The system first sets itself to accept and load the inputs 110. With the reset signal 120 removed from counter 124, the output from clock 122 may now be counted. Clock 122 is selected to operate at 32768 Hz in this particular embodiment and thirty-two pulses, or 1/1024 seconds, is used to encode each data bit.

Counter 124 is composed of two four-bit binary counters, each having a separate input. Clock 122 provides the input to the first counter, designated as $Q^1$. An output 126 is taken from the first counter at the third bit, $Q_3^1$, whereby the leading edge of every fourth input pulse produces a change in state at output $Q_3^1$, as shown in FIG. 4. Signal 126 is provided at the input to the second counter portion, $Q_2$, of counter 124 and also to NAND gate 155. Outputs 127, $Q_1^2$ and 128, $Q_2^2$, are used to form the temporally spaced pulse train as hereinafter described.

During the first system setup cycle, however, signals 127 and 128 are provided to NAND gate 130. It may be seen from FIG. 4 that signals 127 and 128 are both high only during the twenty to twenty-eight pulse count, whereby signal E131 goes low at that time. Signal E131 is also provided to counter 170, which is interconnected to count on a trailing pulse edge, and provides for counting the number of data bits which have been encoded, as hereinafter explained.

Signal E131 is also provided to set-reset circuit 132 and acts to reset output signal D138 high. After the twenth-eighth pulse, E131 returns high, signaling registers 142, 143 and 144 to parallel load inputs 110. At the onset of the encode cycle, signal F136 is already high, causing registers 142, 143 and 144 to operate in the parallel mode.

At the beginning of count 28, it may be seen from FIG. 4 that both $Q_1^2$ and $Q_2^2$ signals 127 and 128, respectively, go low. This causes output A154 from NAND gate 151 and output B156 from NAND gate 152 to go high regardless of the signal on line 140. Thus, all of the input lines to NAND gate 155 are high at count 28, whereby signal C158 goes low. A low going C158 resets circuit 134 to a condition of a low signal F136. Signal F136 remains low throughout the encoding cycle and sets registers 142, 143 and 144 to a serial transfer mode of operation. A low going C158 causes NAND gates 160 to have a high output signal 162, turning on transistors 165 and 166 in current pulse circuit 164 to initiate a current through primary coil 168.

It should be noted that the C158 pulse beginning at count 28 is produced at every cycle of the system and forms the reference pulse for encoding each data bit. At the leading edge of pulse count 32, output $Q_3^1$ 126 from counter 124 goes low, output C158 from NAND gate 155 goes high, output 162 from NAND gates 160 goes low, shutting off transistors 165 and 166 and terminating the current through coil 168. The current rapidly dissipates in resistor R1, producing a rapid collapse in the magnetic field generated by primary coil 168.

The system is now set to begin encoding the data which has been loaded into registers 142, 143 and 144. A first reference spike has been produced and a next output spike must be produced at a time interval functionally related to the binary level of the data in the last gate of the input register 144.

If a high level signal, arbitrarily selected to be a "1", is present on signal line 140, a high signal is presented to NAND gate 151 and a low signal presented to NAND gate 152 through NAND gate 149. In this circumstance, output B156 remains high throughout the cycle, and signal C158 is controlled by outputs $Q_3^1$ and $Q_1^2$ from counter 124. Referring to FIG. 4, it may be seen that signal A154 is high when count $Q_1^2$ 127 is low. Thus, signal C158 will go low only when $Q_3^1$ 126 is high and $Q_1^2$ 127 is low. This event occurs at the leading edge of pulse count 12 and lasts until the leading edge of pulse count 16. The cut-off of output pulse C158 produces the magnetic field decay in primary coil 168, as hereinabove discussed.

Again, signal E131 goes low from count 20 until count 28, incrementing counter 170. When signal E131 goes high at count 28, the data bits in registers 142, 143 and 144 are serially shifted and any data at the serial input line 147 of register 142 is put in the first position in register 142. It may be seen from FIG. 3 that output signal 140 is inverted by NAND gate 146 and available as signal 147 for input back into register 142. Thus, the complement of the data word is stored in registers 142, 143 and 144 as the original command word is serially shifted from the registers.

If signal 140 is low, arbitrarily designated as "0", it may be seen that signal A154 remains high throughout the cycle and a signal C158 output is determined by the outputs of $Q_3{}^1$ and $Q_2{}^2$ from counter 124. The output from NAND gate 149 remains high when signal 140 is low and signal B156 remains high unless $Q_2{}^2$ is low. Signal $Q_2{}^2$ 128 remains low until count 12, whereby signal B156 remains high until count 12. Output $Q_3{}^1$ 126 is concurrently high at the beginning of count 4 until count 8, whereby signal C158 goes low from count 4 until count 8. Again, a low going signal C158 initiates a current in primary coil 168 and the subsequent termination four (4) counts later produces the desired current combination.

Thus, it may be seen that a reference voltage spike is transmitted at the beginning of count 32. If a "1" is encoded, a subsequent voltage spike is transmitted at the beginning of count 16. If a "0" is encoded, the subsequent voltage spike is transmitted at the beginning of count 8.

Thus, the contents of registers 142, 143 and 144 are encoded, reloaded in complementary form and the complements encoded. At the end of 40 data bits, counter 170 acts to terminate the cycle. Counter 170 is a dual 4-bit counter, wherein the fourth bit of the first counter is input to the second counter. Counter 170 is conveniently a binary-coded-decimal counter, wherein output $Q_4{}^1$ occurs every ten counts. Since output $Q_3{}^2$ occurs on a four count, a total of 40 input counts is reached before output $Q_3{}^2$ goes high. On the forty-first count, $Q_1{}^1$ concurrently goes high, producing a low output signal G116 from NAND gate 118. A low signal G116 produces a high signal X120, resetting counter 124. When all of the outputs of counter 124 are reset to a zero level, all events cease. A subsequent reset signal 174 is thereafter applied to set-reset circuit 112, setting reset signal 114 high on counter 170, and signal 115 low, thereby resetting signal D138 and signal F136 to accept a subsequent input 110.

Suitable circuit components for the circuit depicted in FIG. 3 are as follows, wherein reference is made to standard identification code numbers:

| Reference | Identification | Reference | Identification |
|-----------|----------------|-----------|----------------|
| 124 | IC 4520 | R1 | 909 ohms |
| 142 | IC 4014 | R2 | 560 ohms |
| 143 | IC 4014 | R3 | 4.7K ohms |
| 144 | IC 4014 | R4 | 3.9 ohms |
| 165 | TIP 35 | R5 | 3.9 ohms |
| 166 | BU 208 | R6 | 5.6 ohms |
| 170 | IC 4520 | C1 | 2000 μf |

These values are illustrative only and a variety of available components could be selected which are functionally equivalent to the above listed components.

Figure 5:
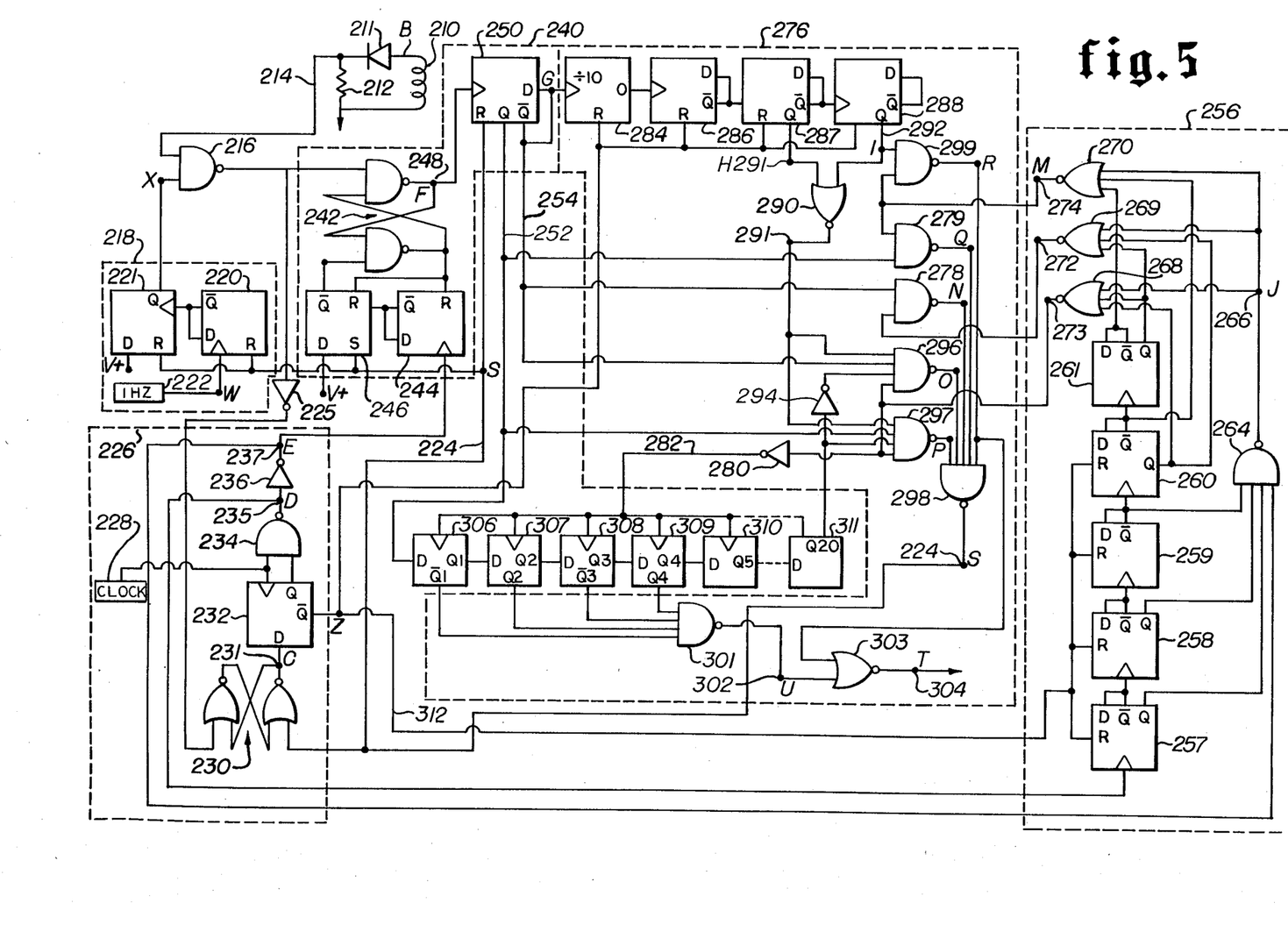
FIG. 5 is a circuit diagram of a decoder.
Figure 6A:
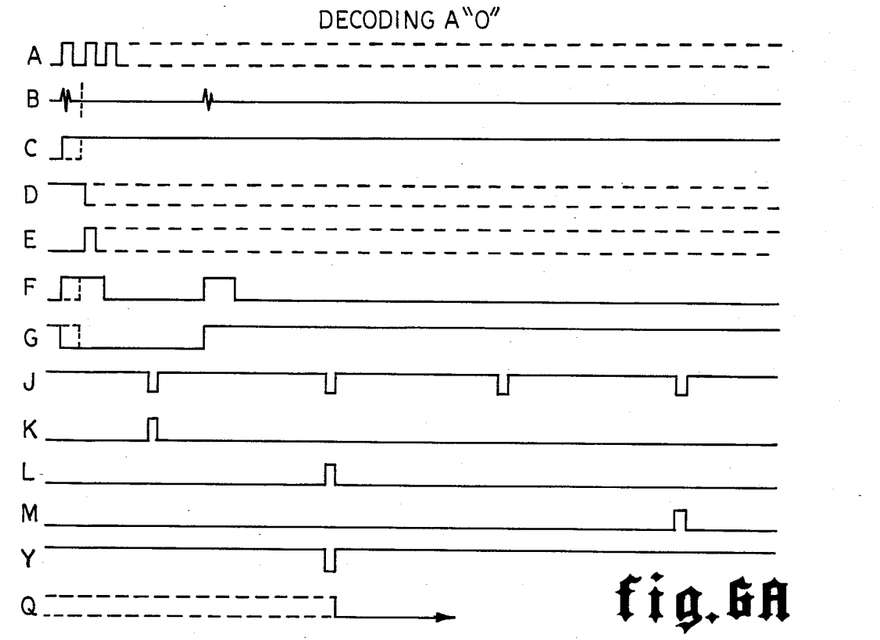
FIG. 6A is a timing diagram for decoding a "0" in the circuit shown in FIG. 5.
Figure 6B:
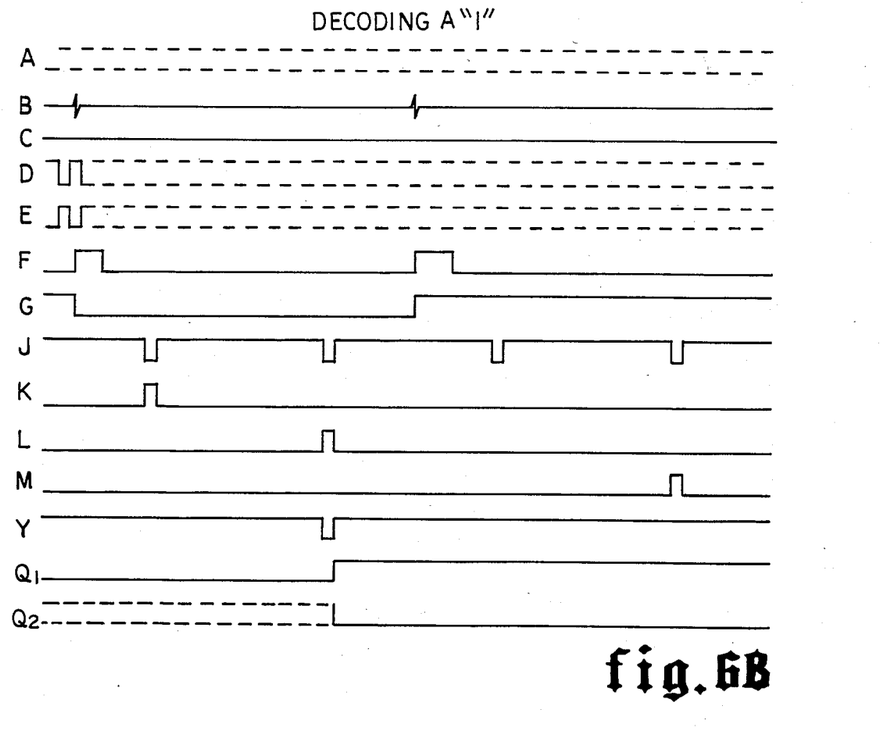
FIG. 6B is a timing diagram for decoding a "1" in the circuit shown in FIG. 5.

Referring now to FIGS. 5, 6A and 6B, there may be seen a preferred embodiment of circuitry for decoding an incoming position modulated pulse train and a timing diagram representing the signal interrelationships at various locations within the circuit. In general, the circuit shown in FIG. 5 acts to inductively receive a transmitted signal at secondary coil 210 and produce a command word at the output of transfer gates 306 through 311, which command word has been verified as accurate prior to the alteration of operating parameter.

As hereinabove explained, the magnetic field produced by the external coil is coupled with the implanted coil 210 through intervening tissue. Coil 210 may conveniently be wound in a flat, oval figuration to save space and in a number of turns selected to obtain the desired output voltage. As the magnetic field produced by the primary coil 168 (see FIG. 3) rapidly collapses at the end of a current pulse, a coupled signal B is produced in secondary coil 210. Signal B is rectified by rectifier 211 and produces output voltage 214 across resistor 212. Input signal 214 does not require that any energy from an implanted battery be expended, since rectifier 211 and resistor 212 are only passive components, requiring no energy. The energy necessary to produce a suitable input signal is wholly supplied by the external signal generator.

Accordingly, input signal 214, which is generally in the form of a voltage spike, is applied to NAND gate 216. NAND gate 216 is enabled to pass the incoming signal 214 by lockout circuit 218. Lockout circuit 218 acts to preclude passing any input signal where an error has been detected in processing a signal, and during an interval after a command word has been received. If an error occurs, signal S224 goes high and resets transfer gates 220 and 221. Once reset, the output from lockout circuit 218 is low and an incoming signal 214 will not produce any change in the output from NAND gate 216. A low frequency clock 222, which may conveniently be 1 Hz, acts to restore an output from lockout circuit 218 once the reset signal 224 is removed. It may be seen from FIG. 5 that output Q from transfer gate 221 will go high after the second clock pulse from clock 222 is input to transfer gate 220.

Incoming signal 214 produces a negative voltage pulse as the output from NAND gate 216, once lockout circuit 218 obtains a high output. The negative pulse goes to pulse generator circuit 240 and to synchronizer circuit 226. The negative going signal acts to set signal F248 to a high state in set-reset circuit 242 and signal F248 remains high until reset as hereinafter explained.

The negative going output from NAND gate 216 is also input through inverter 225 to synchronizer circuit 226. Thus, positive going pulses are used to set circuit 230 to obtain a high output signal C231. The very first incoming signal sets signal C231 to a high level and it remains at a high level until reset by either an error signal or completion of the decoding. The occurrence of a high signal C231 produces a high Q output at the first pulse from internal clock 228 at the clock input to transfer gate 232. Thus, each clock pulse from clock 228 occurring at the input to NAND gate 234 produces a negative going output signal D235 at the same frequency as the clock. Signal D235 passes through inverter 236 to produce signal E237, which is synchronized with internal clock 228 and begins immediately following the first data input spike.

As may be seen from FIGS. 6A and 6B, incoming signal 214 has caused a high level at F248. Further, clock pulses E237 are now being input to transfer gate 244. Transfer gates 244 and 246 form a mini-counter designed to return F248 to a low level after a selected interval. Thus, the output V from transfer gate 246 at $\overline{Q}$ is initially high. A first clock input to transfer gate 244 results in a low output. A second clock input to transfer gate 244 then produces a high input, producing a low $\overline{Q}$ output from transfer gate 246. This output resets the set-reset circuit 242 whereby F248 returns to a low level. Further, transfer gates 246 and 244 are reset at the same time to be ready for another incoming voltage spike.

It is readily apparent, therefore, that signal F248 represents an output synchronized with internal clock 228 but controlled by an external event. Signal F248 forms a position modulated pulse train at a spacing functionally related to the external position modulated pulse train.

Signal F248 becomes the clock input for transfer gate 250 where a data pulse 252 is formed at the Q output. Referring to FIGS. 5 and 6A and 6B, transfer gate 250 normally obtains a high signal G254 at the reset condition. Thus, an incoming clock pulse will transfer signal 254 at the D terminal to output terminal Q to form signal 252. Thus, the leading edge of a first signal F248 pulse will cause a high level output 252 to appear. However, it may be seen that this also results in a low signal G254. The leading edge of the next arriving signal F248 transfers the low level signal G254 to data line 252, which completes the data pulse formation.

Referring to FIGS. 6A and 6B, it may be seen that data signal 252, which is the complement of signal G254, is a width modulated pulse, where the width of the pulse is functionally equivalent to the temporal spacing between adjacent data pulses, generated externally as hereinabove explained. Signal 252 is presented to transfer gate 306 and will be accepted after the data bit is verified, as hereinbelow explained.

While signal 252 is being width modulated, the synchronizer circuit 226 is providing a clock output E237 and a complemented clock output D235 to sample timing circuit 256. Signal D235 is applied to the clock input of transfer gate 257. Transfer gates 257, 258, 259, 260 and 261 form a cascaded counting circuit and are interconnected to produce an output after a preselected number of pulses have been received. In the present embodiment, transfer gates 257, 258 and 259 provide a high input to NAND gate 264 at a count of three, and every four pulses thereafter. Clock pulse E237 is also input to NAND gate 264 wherein a low signal J266 occurs every fourth clock pulse.

The output from transfer gates 260 and 261 are provided to NOR gates 268, 269 and 270, as shown in FIG. 5. Thus, sample circuit 256 provides a high level signal K272 only on the count of four, a high signal L273 only on the count of twelve, and a high signal M274 only on the count of twenty-eight.

Signals K272, L273 and M274 are input to signal verification circuit 276. The basic logic circuit in signal verification circuit 276 consists of NAND gate 278 with output N, NAND gate 296 with output O, NAND gate 297 with output P, NAND gate 279 with output Q, and NAND gate 299 with output R. Outputs N through R remain high until an error signal is received or until data encoding is completed, as hereinbelow explained. The high level signals N through R are applied to NAND gate 298. Thus, output signal S224 from NAND gate 298 is low unless an error is indicated by one of the outputs N through R going low.

A first verification is made on the data bits to insure that a deliberate data bit has been received. At a count of four, signal K272 goes high and is applied to NAND gate 278. As hereinabove explained, a high output level 252 should always occur at a four count regardless of the data bit. Thus, the complement of signal 252, which is signal 254 is compared with signal K272. If signal 254 is correctly low at the four count, output N from NAND gate 278 does not change. In an error condition, output signal 254 would be high at the four count, causing output N from NAND gate 278 to go low, producing a high output signal 224 which resets the entire system and locks out incoming pulses as hereinabove explained.

The next sample time occurs at the twelve count and acts to load the data appearing on data line 252 into transfer gate 306 and shift any data already present in transfer gates 306 through 311. Thus, signal L273 is fed through inverter 280 to form load signal 282 which loads the data on data line 252 and shifts transfer gates 306 through 311 on the trailing edge of the twelve count. A high level signal L273 also appears at the inputs to NAND gates 296 and 297, as hereinbelow explained.

A final data bit verification occurs at the twenty-eighth count. The data on data line 252 will always have a low level on the twenty-eighth count and this condition is detected by applying signal M274 to NAND gate 279. The other input to NAND gate 279 is the signal on data line 252. Thus, if a correct low level is on data line 252, output Q from NAND gate 279 will remain unchanged. In an error condition, a high level output will be present on data line 252, causing output Q from NAND gate 279 to go low, and producing an error signal as hereinabove described.

Thus, each data bit is received, verified, and loaded into transfer gates 306 through 311 to form a first twenty bit word. This word could be used to change the operating parameters of the implanted programmable device, but it is preferred that yet a second check be made of the decoded command word prior to altering the parameters. As hereinabove explained, the external encoder transmits a second twenty bit command word, which is conveniently the complement of the original command word. The decoding system acts to decode the second twenty bit word as hereinabove explained, but also compares each incoming data bit with the corresponding data bit from the original twenty bit word.

The verification circuit 276 first determines that a first twenty data bits have been received and then sets the system to receive a second twenty data bits. A divide-by-ten counter 284 receives an input from signal G254 and provides an output to the clock input of transfer gate 286. Thus, a clock input is provided to counter 284 at the end of each data bit and an input is provided to transfer gate 286 at the end of each tenth data bit. Transfer gate 286 provides an output which forms the clock input to transfer gate 287 which, in turn, provides a clock input to transfer gate 288.

Thus, output signal H291 will appear at the Q terminal of transfer gate 287 immediately following the twentieth data bit. An output signal I292 will appear at terminal Q of transfer gate 288 immediately following the fortieth pulse.

Output signal 291, indicating the beginning of the second twenty bit transmission, is applied to NAND gate 296 and 297. Transfer gates 306 through 311 have been filled by the first data word and the first data bit now appears at the output of the last transfer gate 311. The output level at transfer gate 311 is applied to NAND gate 297 and also inverted by inverter 294 and applied to NAND gate 296. If the data bit in transfer gate 311 is a high, or a "1", NAND gate 297 provides the proper comparison with the incoming signal. Thus, if data line 252 is correctly a zero at the twelfth count, output P from NAND gate 297 will remain high and no error signal is generated. If the data bit at the output of transfer gate 311 is low, or a "0", then the output from inverter 294 will be high. If the data on data line 252 is correctly high, the G254 signal will be correctly low and output 0 from NAND gate 296 will be unchanged. Thus, NAND gates 296 and 297 act to compare the first twenty bit data word with the complement of that data word. If an error occurs during the comparison, a low output from NAND gate 296 or 297 will be obtained, producing an error signal S224 which operates as hereinabove explained.

Once the fortieth data bit has been received, a verified command word of twenty data bits is located in transfer registers 306 through 311. At the end of the fortieth data bit, a high output signal 292 appears at the Q gate of transfer gate 288. Signal 292 is also applied to OR gate 290 for maintaining a high signal on 291, since an output may not be obtained from transfer gate 287 at this time. Thus, a high output signal 292 is applied to NAND gate 299. At the twenty-eighth count, in the fortieth bit, a high level M274 appears also at the input to NAND gate 299 forcing the output R to a low level and generating an output S224. The low-going signal R from NAND gate 299 is also applied to NOR gate 303.

In one operating mode, a final verification is accomplished by encoding the last four data bits in a preselected manner. Thus, the last four data bits must occur in a prearranged sequence before the command word is actually transferred to a command register for altering the output parameters. Outputs from transfer gates 306, 307, 308 and 309 are provided to NAND gate 301 whereby a low output signal U302 occurs if the preselected bit sequence is present. Thus, the inputs to NOR gate 303 are both low, resulting in output signal T304. Signal T304 is applied to a parallel register (not shown) to accept the command word appearing at the output gates ($Q_1$ through $Q_{20}$) of each of registers 306 through 311.

The high signal S224 is also applied to set-reset circuit 230 to terminate clock pulse transmission through synchronizer circuit 226. Further, transfer gates 220, 221, 244, 246 and 250 are all reset to accept the next command word.

As signal C231 goes to a low level, the next pulse from clock 228 to transfer gate 232 produces a high level at $\overline{Q}$ 312. Signal 312 now resets counters 284 and the sample timing gates 257 through 260.

It will be apparent that a variety of circuits could be constructed in accordance with the above teachings to accomplish the various functions described hereinabove. It should also be noted that the specific circuitry may be formed from commercially available integrated circuits or, alternatively, the entire circuit might be specially formed as a single integrated circuit. A single integrated circuit is preferable for an implanted apparatus in order to minimize the bulk associated with that apparatus. If desired, the integrated circuit might include the entire circuit for generating the stimulating pulse corresponding to the operating parameters set by the command word.

It should be apparent from the above description that various of the features in the embodiment of the present invention may have utility in implanted tissue stimulators where an entire command word is not required. Particular features of interest relate to the direct inductive coupling of digital information from an external source to the implanted receiver whereby power consuming demodulation is not required; the use of pulse position modulation to encode binary data; and verifying the accuracy of a completed decoded command word before altering any of the output parameters in response to the command word.

It is therefore apparent that the present invention is one well adapted to attain all of the objects and advantages hereinabove set forth, together with other advantages which will become obvious and inherent from a description of the apparatus itself. It will be understood that certain combinations and subcombinations are of utility and may be employed without reference to other features and subcombinations. This is contemplated by and is within the scope of the present invention. It is to be further understood that all matters hereinabove set forth and shown in the accompanying drawings are to be interpreted as illustrative and not in any limiting sense.

What is claimed is:

1. In a method for varying the operating parameters of a body implantable device by non-invasively coupling an externally generated control signal to electronic circuitry within said implantable device and deriving a binary control word for varying said parameters, an improved method for preventing inadvertent variation of said operating parameters, comprising the steps of:

deriving a first binary word functionally equivalent to a first externally generated control signal, deriving a second binary word functionally equivalent to a second externally generated control signal, said first and second externally generated control signals each functionally related to a same set of selected operating parameters, serially comparing said first and second binary words to verify equivalence, and thereafter transferring said verified binary control word to a command register for altering said operating parameters.

2. The method according to claim 1, wherein comparing said first and second binary words to verify equivalence further comprises the steps of:

storing said first binary word in a first serial register, serially comparing said first binary word and said second binary word, and storing said second binary word in said first serial register.

3. The method according to claim 2, wherein said first binary word is serially output from said first register as said second binary word is serially input to said first register.

4. The method according to claims 1 or 2, including the step of:

deriving said second binary word as the complement of said first binary word.

5. In apparatus for varying the operating parameters of a body implantable device by non-invasively coupling an externally generated control signal to electronic circuitry within said device and deriving a binary control word for varying said operating parameters, improved apparatus for preventing inadvertent variation of said operating parameters, comprising:

means for deriving a first binary word functionally equivalent to a first externally generated control signal, means for deriving a second binary word functionally equivalent to a second externally generated control signal, said first and second externally generated control signals each functionally related to a same set of selected operating parameters, means for serially comparing said first and second binary words to verify equivalence, and electronic circuitry for transferring said verified binary control word to a command register for altering said operating parameters.

6. Apparatus according to claim 5, wherein said means for comparing said first and second binary words to verify equivalence further comprises:

a first serial register for storing said first binary word, means for serially comparing said first binary word and said second binary word, and a second serial register for storing said verified binary control word.

7. Apparatus according to claim 6, including means for serially removing said first binary word from said first register as said second binary word is serially input to said second register.

8. Apparatus according to claims 6 or 7, wherein said first register and said second register comprise a single register.

9. Apparatus according to claims 5 or 6, including:

means for deriving said second binary word as the complement of said first binary word.

10. Apparatus for commanding a body function stimulating device adapted for body implantation, comprising:

means for generating an electrical command signal functionally related to selected operating parameters for said stimulating device;

means for converting said electrical command signal to an equivalent train of current pulse pairs having first or second temporal relationships and each pulse having at least one sharp edge shape;

a first coil means responsive to said current pulse pairs generating magnetic fields having a peak rate of change of intensity defined by said at least sharp edge shape of each said pulse;

a second coil means electrically connected to said stimulating device detecting at least said peak rate of change of intensity portions of said magnetic fields and producing corresponding pairs of voltage output pulses having said first or second temporal relationship;

means for processing said pairs of voltage output pulses to reproduce said electrical command signal within said stimulating device.

11. Apparatus according to claim 10, wherein said means for processing said pairs of voltage output pulses comprises:

means for generating single pulses from said pairs of voltage pulses having first and second durations corresponding to said first and second temporal relationships, respectively.

12. Apparatus according to claim 11, comprising:

means for gating each of said single pulses at first preselected intervals, and means for generating a data signal having a binary output determined by the output level of said single pulse during said gating at said first interval.

13. Apparatus according to claim 12, further comprising:

means for detecting the level of said single pulses at second preselected intervals to verify the absence of anomalies in said single pulse.

14. Apparatus according to one of claims 10, 11, 12, or 13, wherein said first temporal relationship represents a first binary state and said second temporal relationship represents a second binary state.

15. Apparatus according to one of claims 10, 11, 12, or 13, further including:

means for generating first and second portions of said electrical command signal functionally related to said selected operating parameters, means for decoding said first portion of said electrical command signal and generating a corresponding first binary word within said stimulating device, means for decoding said second portion of said electrical command signal and generating a corresponding second binary word within said stimulating device; and means for serially comparing said second binary word with said first binary word and upon determining the equivalence of the binary words applying one of the words to set said selected operating parameters for the stimulating device.

16. Apparatus according to claim 15, including: means for generating said second portion of said electrical command signal as functionally equivalent to a binary complement of said first portion of said electrical command signal.

17. A method for commanding a body function stimulating device adapted for body implanatation, comprising the steps of:

generating an electrical command signal functionally related to selected operating parameters for said stimulating device;

converting said electrical command signal to an equivalent train of current pulse pairs having first or second temporal relationships and each pulse having at least one sharp edge shape;

generating magnetic fields in response to said current pulse pairs having a peak rate of change of intensity defined by said at least one sharp edge shape of each said pulse;

detecting within said stimulating device at least said peak rate of change of intensity portions of said magnetic fields and producing corresponding pairs of voltage output pulses having said first or second temporal relationship;

processing said pairs of voltage output pulses to reproduce said electrical command signal within said stimulating device.

18. A method according to claim 17, wherein processing said pairs of voltage output pulses comprises:

generating single pulses from said pairs of pulses having first and second durations corresponding to said first and second temporal relationships, repsectively.

19. A method according to claim 18, comprising:

gating each of said single pulses at first preselected intervals, and generating a data signal having a binary output determined by the output level of said single pulse during said gating at said first interval.

20. A method according to claim 19, further comprising:

detecting the level of said single pulses at second preselected intervals to verify the absence of anomalies in said single pulses.

21. A method according to one of claim 17, 18, 19, or 20, wherein:

said first temporal relationship represents a first binary state and said second temporal relationship represents a second binary state.

22. A method according to one of claims 17, 18, 19, or 20, further including the steps of:
generating first and second portions of said electrical command signal functionally related to selected operating parameters,
decoding said first and second portions and repsectively generating corresponding first and second binary words within said stimulating device, and serially comparing said first binary word and said second binary word and setting said selected operating parameters upon determining the equivalence of the words.

23. A method according to claim 22, including:
generating said second portion of said electrical command signal as functionally equivalent to a binary complement of said first portion of said electrical command signal.

24. In apparatus for varying the operating parameters of a body function stimulating device adapted for body implantation by non-invasively coupling an externally generated control signal to electronic circuitry within said implantable device and deriving a control signal for varying said parameters, improved apparatus for transmitting said control signal, comprising:
means for generating an electrical command signal functionally related to selected operating parameters for said stimulating device;
means for converting said electrical command signal to an equivalent train of current pulse pairs having first or second temporal relationships, said first temporal relationship corresponding to a first binary state and said second temporal relationship corresponding to a second binary state;
means for generating an output functionally related to said pulse pairs;
means for detecting said output and producing corresponding pairs of voltage output pulses having said first and second temporal relationship; and
means for processing said pairs of voltage output pulses to reproduce said electrical command signal within said stimulating device.

25. Apparatus according to claim 24, wherein said means for processing said pairs of voltage output pulses comprises:
means for generating single pulses from said pairs of voltage pulses having first and second durations corresponding to said first and second temporal relationships, respectively.

26. Apparatus according to claim 25, comprising:
means for gating each of said single pulses at first preselected intervals, and
means for generating a data signal having a binary output determined by the output level of said single pulse during said gating at said first interval.

27. Apparatus according to claim 26, further comprising:
means for detecting the level of said single pulses at second preselected intervals to verify the absence of anomalies in said single pulses.

28. In a method for varying the operating parameters of a body function stimulating device adapted for body implantation by non-invasively coupling an externally generated control signal to electronic circuitry within said implantable device and deriving a control signal for varying said parameters, an improved method for generating said command signal, comprising the steps of:
generating an electrical command signal functionally related to selected operating parameters for said stimulating device;
converting said electrical command signal to an equivalent train of current pulse pairs having first or second temporal relationships, said first temporal relationship corresponding to a first binary state and said second temporal relationship corresponding to a second binary state;
generating an output functionally related to said pulse pairs;
detecting said output;
producing corresponding pairs of voltage output pulses having said first or second temporal relationship; and
processing said pairs of voltage output pulses to reproduce said electrical command signal within said stimulating device.

29. A method according to claim 28, wherein said means for processing said pairs of voltage output pulses comprises:
generating single pulses from said pairs of pulses having first and second durations corresponding to said first and second temporal relationships, repsectively.

30. A method according to claim 29, comprising:
gating each of said single pusles at first preselected intervals, and
generating a data signal having a binary output determined by the output level of said single pulse during said gating at said first interval.

31. A method according to claim 30, further comprising:
detecting the level of said single pulses at second preselected intervals to verify the absence of anomalies in said single pulses.

32. A system for communicating parameter control information from a control device to a body implantable device, comprising:
select means of said control device for defining parameter control information;
coding means of said control device for generating binary coded pulse position modulated signals representative of said defined parameter control information; and
transmitter means of said control device for transmitting said binary coded pulse position modulated signals to said body implantable device;
receiving means of said body implantable device for receiving said binary coded pulse position modulated signals and decoding said signals to derive said parameter control information, and operating means of said body implantable device for applying said derived parameter control information to operate the device.

33. The system of claim 32, wherein said transmitter means includes a transmitter coil; and said coding means includes:
means for defining an output parameter code word having a plurality of binary bits representative of said defined parameter control information; and
means for producing and applying current pulses to said transmitter coil, said current pulses having edges spaced at intervals representative of said binary bits of said output parameter code word so that the transmitter coil transmits electromagnetic pulses spaced with corresponding intervals.

34. The system of claim 33, wherein said receiving means includes:
receiving coil means for generating voltage pulses at intervals corresponding to the intervals of said electromagnetic pulses;
decoding means for generating synchronized signals with pulse widths corresponding to the intervals between the voltage pulses; and
sampling means for generating an input parameter code word having binary bits representative of the pulse widths of the synchronized signals and corresponding to the bits of the output parameter code word,
said operating means including means for applying the input parameter code word to control said implantable device.

35. The apparatus of claim 34, wherein said sampling means includes means for checking predefined portions of said synchronized signals to determine whether the signals have electrical anomalies.

36. The apparatus of claim 34, wherein said means for defining includes means for generating an output parameter check word with binary bits which are the complement of the bits of said output parameter code word, said means for producing and applying current pulses including means for applying edges of current pulses to said transmitter coil at intervals representative of the binary bits of the parameter check word, so that the transmitter coil transmits electromagnetic pulses spaced at corresponding intervals,
said sampling means including means for generating an input parameter check word having bits corresponding to the bits of the output parameter check word, and means for comparing the input parameter code word and input parameter check word to determine if they match as complements, said means for applying control data including means for applying the input parameter code word to control the implantable device in the event of a match.

37. A system for communicating parameter control information to a body stimulation device implanted in the body, comprising:
transmitter means outside the body for transmitting binary coded pulse position modulated electromagnetic signals representative of selected parameter control information;
means of said body stimulation device for receiving said electromagnetic signals and decoding the signals to derive at least one binary coded word representative of said selected parameter control information;
means of said body stimulation device for verifying the validity of said at least one binary word; and
means of said body stimulation device for applying the verified binary coded word to set at least one operating parameter of the body stimulation device.

38. The system of claim 37, wherein said transmitter means includes means for transmitting electromagnetic signals representative of said binary coded word and its binary complement,
said means for receiving including means for decoding the electromagnetic signals to derive said binary coded word and its binary complement, and
said means for verifying includes means for comparing the binary coded word and its binary complement.

39. The system of claim 37, wherein said means for verifying includes means for checking predefined signal portions of said at least one binary coded word to verify that the signal portions have no electrical anomalies.

40. A system for communicating selected parameter control information from a control device to a body implatable device, comprising:
transmitter means of said control device for generating electromagnetic pulses spaced at intervals representative of binary bits which define said selected parameter control information;
receiving means of said body implantable device for detecting said electromagnetic pulses and generating derived pulses having widths corresponding to the intervals between the electromagnetic pulses;
means of said body implantable device for converting the pulse widths of the derived pulses to binary logic signals representative of said selected parameter control information; and
means of said body implantable device for applying the binary logic signals to control selected parameters of the implantable device.

41. A system for communicating selected parameter control information from a control device to a body implantable device, comprising:
coding means of said control device for generating current pulses having edges spaced at intervals representative of selected parameter control information;
and transmitting coil means of said control device for transmitting an output signal for each of the spaced edges of said current pulses,
said body implantable device including,
receiving coil means for detecting each of said output signals and generating a corresponding input signal,
means for decoding the intervals between input signals to derive control signals representative of said selected parameter control information, and
means for applying said control signals to control the operation of said implantable device.

42. A system for communicating selected parameter control information from a control device to a body implantable device, comprising:
coding means of said control device for generating signals having trailing edges spaced at intervals representative of said selected parameter control information;
a transmitter coil of said control device for transmitting an electromagnetic pulse for each of said trailing edges;
a receiver coil of said control device for sensing said electromagnetic pulses and generating corresponding voltage pulses; and
means of said body implantable device responsive to the intervals between said voltage pulses for deriving the selected parameter control information and applying the information to control the implantable device.

43. A body implantable device, comprising:
means for receiving binary coded pulse position modulated signals representative of parameter control information;
means for decoding said binary coded pulse position modulated signals to derive said parameter control information; and
means for applying said parameter control information to set operating parameters of said body implantable device.

* * * * *